US006320035B1

(12) United States Patent
Mühlegger et al.

(10) Patent No.: US 6,320,035 B1
(45) Date of Patent: Nov. 20, 2001

(54) C-NUCLEOSIDE DERIVATIVES AND THEIR USE IN THE DETECTION OF NUCLEIC ACIDS

(75) Inventors: Klaus Mühlegger, Polling; Herbert Von Der Eltz, Weilheim; Frank Seela; Helmet Rosemeyer, both of Osnabrück, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/695,210

(22) Filed: Oct. 25, 2000

Related U.S. Application Data (60) Division of application No. 08/929,068, filed on Sep. 15, 1997, now Pat. No. 6,174,998, which is a continuation-in-part of application No. PCT/EP96/01051, filed on Mar. 12, 1996.

(30) Foreign Application Priority Data

Mar. 14, 1995 (DE) ................................. 195 09 038

(51) Int. Cl.$^7$ .............................. C12Q 1/68; C07H 19/00; C07H 21/00; C07H 21/02; C07H 21/04
(52) U.S. Cl. ...................... 536/23.1; 536/22.1; 536/24.3; 536/24.33; 536/25.3; 536/25.34; 536/26.26; 536/26.71; 536/26.8; 435/6; 435/91.1; 435/91.2
(58) Field of Search .............................. 536/22.1, 23.1, 536/24.3, 24.33, 25.3, 25.34, 26.26, 26.71, 26.8; 435/6, 91.1, 91.2

(56) References Cited

U.S. PATENT DOCUMENTS 5,728,525    3/1998    Conrad .

FOREIGN PATENT DOCUMENTS 0 135 587    2/1990    (EP) .

OTHER PUBLICATIONS

Biochemistry, vol. 13, No. 17, 1974 pp 3615–3621; "Covalent Attachment of fluorescent Groups to Transfer Ribonucleic Acid. Reactions with 4–Bromomethyl–7–methoxy–2–oxo–2H–benzopyran", Yang, et al.

Nucleosides & Nucleotides, 13(8), pp 1721–1738 (1994); "A Facile Synthesis of the Phosphor Amidites of 2–N–Methyl–2'–Deoxy (or 2'–O–Allyl)–Ψ–Isocytidine, 1,3–Dimethyl–2'–Deoxy–Ψ–Uridine and N1–Methyl–2'–O–Allyl–Ψ–Uridine as Synthons Suitable for Oligonucleotide Synthesis", Bhattacharya, et al.

Nucleosides & Nucleotides, 12(3&4), pp 381–401 (1993); "Synthesis of Oligodeoxynucleotides Containing the C–nucleoside and 2'–Deoxy–2'–Fluoro–ara–Nucleoside Moieties by the H–Phosphonate Method", Rosenberg, et al.

J. Heterocyclic Chem., 14, 1119–1121 (1977); "Nucleosides. CIX. 2'–Deoxy–105 –isocytidine, 2'–Deoxy–Ψ–uridine, and 2'–Deoxy–1–methyl–Ψurdine. Isosteres of deoxycytidine, Deoxyuridine and Thymidine", Chu, et al.

Sato et al., "Stereocontrolled sy nthesis of 1', 4–dialkylated pyrimidine ribo–c–nucleosides", Chem istry letters, pp. 679–682, 1980.

Lim et al., "Synthesis of 9–Deazaguanosine and other new py rrolo[3,2–d]pyrimidine c–nucleosides", J. Org. Chem., pp. 780–788, vol. 48, 1983.

Ugarkar at al., "A simple oxidatipon of formycin to oxoformycin and oxoformycin B. Synthesis of 6–methyloxoformycin, a c–nucleoside of doridosine", J. Heterocy clic Chem., vol. 21, pp. 1865–1869, 1984.

Serafinowski, "Synthesis of S–formycinyl–L–homocysteine and its 3'–deox y derivative", Synthesis, pp.879–883, 1987.

Primary Examiner—Jezia Riley
(74) Attorney, Agent, or Firm—Arent Fox Kintner Plotkin Kahn, PLLC

(57) ABSTRACT

The invention concerns pyrrolo-[3,2-d]pyrimidine, pyrazolo-[4,3-d]pyrimidine and pyrimidine-furanosides i.e. so-called C-nucleosides of the general formulae I–V

I

II

III

-continued

IV

V or appropriate derivatives as well as processes for their production.

50 Claims, 1 Drawing Sheet

C-NUCLEOSIDE DERIVATIVES AND THEIR USE IN THE DETECTION OF NUCLEIC ACIDS

This is a Division of Application No. 08/929,068 filed Sep. 15, 1997, which is a Continuation-In-Part of International Application Serial No. PCT/EP96/01051, filed Mar. 12, 1996, and designating the U.S. The disclosure of the prior application(s) is hereby incorporated by reference herein in its entirety.

The compounds are in particular suitable as substrates for RNA or DNA polymerases and can thus be incorporated into RNA or DNA oligonucleotides. Therefore the compounds are especially suitable for labelling and for detecting nucleic acids and for DNA sequencing.

The invention concerns C-nucleosides and derivatives thereof as well as their use for labelling, detecting and sequencing nucleic acids.

Nucleic acids are of central importance in living nature as carriers or transmitters of genetic information. Therefore since their discovery by F. Miescher they have stimulated a broad scientific interest which has led to the elucidation of their function, structure and mechanism of action. The increasing knowledge of these basic mechanisms in molecular biology has made it possible in recent years to make new combinations of genes. This technology opens for example new opportunities in medical diagnosis and therapy and in plant breeding.

An important tool for elucidating these relationships and to solve problems was and is the detection of nucleic acids with regard to their specific detection as well as with regard to their sequence i.e. their primary structure.

The specific detectability of nucleic acids is based on the property of these molecules to interact or hybridize with other nucleic acids by forming base pairs via hydrogen bridges. Nucleic acids (probes) labelled in a suitable manner i.e. provided with indicator groups, can thus be used to detect complementary nucleic acids (target).

The determination of the primary structure (sequence), i.e. the sequence of the heterocyclic bases of a nucleic acid, is carried out by means of sequencing techniques. This knowledge of the sequence is in turn a prerequisite for a targetted and specific use of nucleic acids in problems and methods of molecular biology. In the end sequencing also utilizes the specific hybridization among nucleic acids. Labelled nucleic acid fragments are also used for this as mentioned above.

Consequently the suitable labelling of nucleic acids is an indispensable prerequisite for any detection method.

Radioactive labelling with suitable isotopes such as $^{32}P$ or $^{35}S$ was already used for this at an early stage. The disadvantages of using radioactive reagents are, however, obvious: such work requires specially equipped facilities and permits as well as a controlled and complicated disposal of the radioactive waste. Furthermore the reagents for radioactive labelling are expensive. It is not possible to store such labelled samples for long periods due to the short half-lives of the above nuclides.

In recent years there have therefore been many attempts to circumvent these serious disadvantages i.e. to get away from radioactive labelling. In doing so the high sensitivity of this type of label should be retained as far as possible.

Major advances have in fact already been achieved [see for example Nonradioactive Labeling and Detection of Biomolecules (Kessler, C., pub.) Springer Verlag, Berlin, Heidelberg 1992].

An essential prerequisite for any detection of a nucleic acid is that it should be previously labelled and—as explained above—if possible in a non-radioactive manner. Whereas the radioactive labelling of nucleic acids is usually carried out by enzymatically catalysed incorporation of corresponding radioactive nucleoside triphosphates, non-radioactive labelling must be achieved by incorporating a suitable signal or reporter group.

Non-radioactive indicator molecules that have proven to be suitable among others are above all haptens (such as biotin or digoxigenin), enzymes (such as alkaline phosphatase or peroxidase) or fluorescent dyes (such as fluorescein or rhodamine). These signal groups can be attached to or incorporated into nucleic acids by various methods.

A relatively simple procedure is for example to label the 5' end of an oligonucleotide provided with a terminal amino function by means of activated indicator molecules of the above-mentioned type. However, this only enables one or a few indicator molecules to be introduced into only a low molecular oligomer whereas a denser labelling of longer chained, high molecular nucleic acids with the goal of achieving a higher sensitivity must usually be achieved by incorporating nucleoside triphosphates provided with reporter groups by means of polymerases along the lines of a de novo synthesis.

Corresponding methods are known to a person skilled in the art as nick translation [Rigby, P. W. et al. (1977), J.Mol.Biol. 113, 237] and random primed labelling [Feinberg, A. P. & Vogelstein. B. (1984) Anal. Biochem. 137, 266]. A further method is the so-called 3'-tailing reaction with the aid of the enzyme terminal transferase.

The nucleoside triphosphates which have been used up to now in these methods are almost exclusively appropriately modified derivatives of the heterocyclic bases adenine, guanine, cytosine and thymine in the deoxyribonucleotide series, or adenine, guanine, cytosine and uracil in the ribonucleotide series. Such derivatives are for example described by Langer et al., Proc. Natl. Acad. Sci. USA 78, 6635 (1981); Mühlegger et al., Biol. Chem. Hoppe-Seyler 371, 953 (1990) and in EP 0 063 879. In this case the building blocks that occur naturally in DNA and RNA are used in a labelled form i.e. in a form provided with signal groups. The main disadvantages of the N-nucleosides are the sensitivity of the N-glycosidic bond towards acidic pH conditions and degradability by nucleases.

Furthermore individual C-nucleosides (see e.g. Suhadolnik, R. J. in Nucleoside Antibiotics, Wiley-Interscience, New York 1970) and their therapeutic use (antiviral or cancerostatic) has been known for a long time.

In addition fluorescent C-nucleoside derivatives and their incorporation into DNA and RNA oligonucleotides has been described (WO 93/16094). The so-called inherent fluorescence of these C-nucleosides is, however, many-fold less with regard to quantum yield than of special fluorophores such as fluorescein or corresponding rhodamine derivatives. A further disadvantage of the autofluorescent C-nucleosides is their relatively low excitation and emission wavelengths. As a consequence detection systems which are based on such derivatives only have a low detection sensitivity and on the other hand spectrally interfering influences of the measurement environment (such as biological material, autofluorescence of gel matrices etc.) become very apparent.

The known nucleosides and nucleoside derivatives thus have a number of disadvantages which in particular have adverse effects on the detection of nucleic acids.

Hence the object of the invention is to provide nucleoside derivatives modified with signal groups for the detection of nucleic acids which do not have the said disadvantages i.e. are in particular more stable and at the same time able to be processed enzymatically and are suitable for the detection of nucleic acids at a more practical wavelength.

The object is achieved by pyrrolo-[3,2-d]pyrimidine, pyrazolo-[4,3-pyrimidine and pyrimidine-furanosides of the general formulae I-V:

in which $R_1$, $R_2$, $R_3$, $R_4$ can be same or different and represent hydrogen, halogen, hydroxy, thio or substituted thio, amino or substituted amino, carboxy, lower alkyl, lower alkenyl, lower alkinyl, aryl, lower alkyloxy, aryloxy, aralkyl, aralkyloxy or a reporter group, $R_5$ and $R_6$ each represent hydrogen, hydroxy, thio or substituted thio, amino or substituted amino, lower alkyloxy, lower alkenoxy, lower alkinoxy, a protecting group or a reporter group, $R_7$ represents hydrogen, hydroxy, thio or substituted thio, amino or substituted amino, a phosphoramidite or H-phosphonate group, an ester or amide residue that can be cleaved in a suitable manner or a reporter group, $R_6$ and $R_7$ together form a further bond between C-2' and C-3' or an acetal group, $R_8$ represents hydrogen or a hydroxy, thio or substituted thio, amino or substituted amino group, $R_9$ represents hydrogen, a mono-, di- or triphosphate group or the alpha, beta or gamma-thiophosphate analogues of these phosphoric acid esters or a protecting group, as well as possible tautomers and salts thereof.

Any detectable groups come into consideration as a reporter group such as in particular haptens, a fluorophore, a metal-chelating group, a lumiphore, a protein or an intercalator.

Those compounds of the general formulae I to V are preferred in which the acetal function of the residues $R_6$ and $R_7$ is substituted by a reporter group.

Furthermore those compounds have proven to be particularly suitable in which the reporter group is bound to the aglyconic or furanose ring via a so-called linker group. Appropriate linker groups are known to a person skilled in the art (see e.g. Mühlegger, K. et al. (1990) Biol. Chem. Hoppe-Seyler 371, 953–965 or Livak, K. J. et al. (1992) Nucl. Acids Res. 20, 4831–4837).

In addition compounds of the general formulae I to IV are preferred in which $R_1$ represents hydrogen, hydroxy or an amino group, $R_2$ represents hydroxy, an optionally substituted amino group or a reporter group, $R_3$ and $R_4$ represent hydrogen, halogen or a reporter group, $R_5$ represents hydrogen, $R_6$ represents hydrogen or hydroxy, $R_7$ represents hydrogen, hydroxy, thio, an optionally substituted amino group, a phosphoramidite or a reporter group, $R_6$ and $R_7$ together represent an acetal function, $R_8$ represents hydrogen and $R_9$ represents a triphosphate function.

Preferred compounds of the general formula V are those in which $R_1$ represents hydroxy, a thio or amino group which optionally can be substituted or a reporter group, $R_2$ and $R_3$ represent hydrogen, lower alkyl or a reporter group, $R_5$ represents hydrogen, $R_6$ represents hydrogen or hydroxy, $R_7$ represents hydrogen, hydroxy, thio, an optionally substituted amino group, a phosphoramidite or a reporter group, $R_6$ and $R_7$ together represent an acetal function, $R_8$ represents hydrogen and $R_9$ represents a triphosphate function.

It is expedient to synthesize the new modified C-nucleosides by starting with naturally occurring precursors. Thus for example formycin A as an adenosine analogue can be deaminated to form formycin B (an inosine analogue). This can in turn be halogenated and be further substituted nucleophilically by which means it is possible to produce a series of interesting new compounds such as those of the inventive type.

The important 2'-deoxy-nucleosides are synthesized by deoxygenating the above-mentioned naturally occurring ribonucleosides such as e.g. formycin A. In this case the deoxygenation reaction according to Barton is mainly used nowadays (Barton, D. H. R. & Motherwell, W. B. (1981) Pure Appl. Chem. 53, 15).

Furthermore the C-nucleosides can be synthesized chemically as described for example in detail by K. A. Watanabe in "Chemistry of Nukleosides and Nukleotides" 3, 421–535 (L. B. Townsend, publ.) Plenum Press, New York and London, 1994.

The use of the compounds according to the invention to label nucleic acids with diverse defined signal groups and thus to detect and sequence nucleic acids has proven to be particularly advantageous.

The C-nucleosides according to the invention of the general formulae I to V have a number of advantages especially compared to the classical N-glycosidically linked nucleosides and nucleotides such as adenosine, guanosine, cytidine, thymidine, uridine and corresponding phosphoric acid esters thereof.

One advantage is the chemical stability of the C-glycosidic bond for example towards acidic pH conditions. A further important advantage is the stability of these compounds towards enzymatic degradation by endonucleases and exonucleases. These enzymes are present in biological material and can severely interfere with the nucleic acid detection. On the other hand it is known that DNA and RNA polymerases are very discriminating with regard to accepting nucleoside 5'-triphosphates that have been modified to a greater or lesser extent i.e. with regard to recognizing and incorporating such nucleotides as substrates in the de novo synthesis. In particular experience has shown that the attachment of signal groups to nucleotides influences the incorporation and incorporation rate.

The fact that the nucleosides according to the invention and derivatives thereof are incorporated very efficiently into nucleic acids by suitable polymerases such as e.g. by the methods described above of nick translation or of random primed labelling cannot be easily inferred from the state of the art and it must thus be regarded as surprising for a person skilled in the art.

The said methods are generally used in nucleic acid detection e.g. for the quantitative detection by blotting techniques on membranes or also in microtitre plates.

In the sequencing i.e. the detection of the sequence of a nucleic acid, a complementary opposite strand is newly synthesized on the nucleic acid to be sequenced with the aid of a short (start) oligonucleotide (primer) and a polymerase.

In the in situ hybridization for the detection of certain genes or genome sections the same basically occurs in the cell i.e. the specific incorporation of labelled nucleotides.

The above-mentioned primers i.e. short-chained oligonucleotides should form stable base pairs with the template strand as well as not be attacked by endogenous nucleases in order to ensure an optimal function.

This is fulfilled by oligonucleotides which contain the C-nucleosides according to the as building blocks invention instead of the classical N-nucleosides.

The same applies to long-chained polynucleotides and nucleic acids which contain such C-nucleoside building blocks. These are also a subject matter of the present invention.

Corresponding oligonucleotides as well as their preparative precursors the nucleoside phosphoramidites and nucleoside H-phosphonates are therefore also a subject matter of the invention.

Nowadays oligonucleotides are usually synthesized by known methods in automated DNA/RNA synthesizers.

Such methods of synthesis are essentially based on the step-wise reaction of the above-mentioned phosphoramidites or H-phosphonates and thus the continuous linkage of these monomeric building blocks to form oligomers (see e.g. T. Brown & D. J. S. Brown in Oligonucleotides and Analogues-A Practical Approach (1991) (Eckstein. F., publ.), IRL Press at Oxford University Press, Oxford, New York, Tokyo).

Legend 5

FIG. 1

I and II denote pBR 328 DNA labelled by DIG-dUTP incorporation and III denotes pBR 328 DNA labelled by DIG-3-O-succinyl-ε-amino-caproyl-[7-amino-3-(2'-deoxy-β-D-erythropento-furanosyl)-1H-pyrazolo-[4,3-d]-pyrimidine-5'-triphosphate incorporation.

Preferred embodiments of substituted thio groups include alkylthio-$(CH_2)_n$—SH with n=1–10, and thioalkyl-S—$(CH_2)_nCH_3$ with n=0–10.

Preferred embodiments of substituted amino groups include alkylamino-$(CH_2)_n$—NH2 with n=1–15, alkylamido-$(CH_2)_nC$=O—NH— with n=1–15,-aminoalkyl—NH—$(CH_2)_n$CH3 with n=0–15,aminoalkyl-amino-NH—$(CH_2)_n$NH— with n=1–15, alkenylamino—CH=$(CH_2)_n$—NH— with n=1–6, and alkinylamino-C≡C—$(CH_2)_n$—NH— with n=1–10.

As used in the present document, the term lower alkyl is intended to mean alkyl with $C_1$–$C_6$, lower alkenyl means alkenyl with $C_2$–$C_6$, lower alkinyl means alkinyl with $C_2$–$C_6$, and lower alkyloxy means alkyloxy-O—$(CH_2)_nCH_3$ with n=0–6. The preferred aryloxy group is aryloxy with —O—$C_6H_6$, the preferred aralkyl is aralkyl with —$(CH_2)_nC_6H_6$ with n=1–6, the preferred aralkyloxy is aralkyloxy-O—$(CH_2)_nC_6H_6$ with n=1–6, and the preferred aryl is aryl with $C_6H_5$—. The preferred lower alkenoxy is —O-alkenyl with $C_2$–$C_6$, and the preferred lower alkinoxy is —O-alkinyl with $C_2$–$C_6$. The preferred protecting groups are —O-acetyl, —O-benzoyl and —O-mesyl.

Examples of ester or amide residues which can be cleaved include —O—C=O and —NH—C=O-which can be chemically or enzymatically cleaved.

The syntheses of the oligonucleotides according to the H-phosphonate method comprises the following steps:

a) synthesis of an oligonucleotide chain on a solid support by stepwise coupling of the appropriate activated nucleoside-3'-H-phosphonate, b) oxidation of the trivalent phosphorus to the pentavalent derivative and cleavage from the solid support at the end of the synthesis.

This method is described by Froehler, B. C. in "Protocols for Oligonucleotides and Analogs", Vol. 20, page 63 in "Methods in Molecular Biology", Humana Press, Inc., Totowa, U.S.A.

The synthesis of Oligonucleotides according to the phosphoramidite process comprises the following steps:

a) synthesis of an oligonucleotide chain on a solid carrier by stepwise linking of the appropriate nucleoside-phosphoramidites, b) after every linking step the internucleotide binding of the trivalent phosphate is oxidized to pentavalent phosphate, c) after synthesis the oligonucleotide is cleaved from the solid carrier.

The above described oligonucleotidesynthesis is well known to a person skilled in the art prior to the priority date of the present invention (Caruthers and Beaucage, (1981), Tetrah. Lett. 22, p. 1859; Beaucage, S. L. in Protocols for Oligonucleotides and Analogs", Vol. 20, p 33 in, "Methods in Molecular Biology". Humana Press, Inc. Totowa, USA 1993; Agrawal, S. in "Protocols for Oligonucleotides and Analogs" Vol. 26, p. 93 of the series "Methods in Molecular Biology", Humana Press, Inc., Totowa, USA 1994).

Methods for detecting nucleic acids, sequencing DNA, and in situ hybridization are well known in the art as evidenced by Sambrook et al., Molecular Cloning, A Laboratory Manual, 2nd ed., Cold Spring Harbor Laboratory Press, 1989.

The invention is elucidated in more detail by the following examples.

EXAMPLE 1

$N^1$-Carboxymethyl-7-amino-3-($\beta$-D-erythro-pentofuranosyl)-1H-pyrazolo-[4,3-d]-pyridimine 70 mg (0.25 mmol) formycin A, 400 mg (2.2 mmol) ethyl iodoacetate and 400 mg (2.88 mmol) $K_2CO_3$ are stirred in 5 ml methanol/water (1:1) for 3 h at room temperature. The solution is subsequently evaporated to dryness, taken up in 4 ml $H_2O$ and chromatographed on a preparative HPLC (RP-18,25×1 cm). Water elutes ($R_F$=7 min) a main zone which is collected and concentrated by evaporation. After lyophilization one obtains 48 mg of the title compound (59%).

$^1$H-NMR ($D_2O$): 7.98 (s, H-5); 5.02 (d, J=7.4 Hz, H-1'); 4.95 (s, $CH_2$); 4.46 (t=6.0 Hz, H-2'); 4.21 (t, J=3.5 Hz, H-3'); 4.07 (d, J=2.7 Hz, H-4'); 3.70 (m, $H_2$-5'). $^{13}$C-NMR ($D_2O$): 174.4 (C=O); 151.8 (C-7); 151.6 (C-5); 141.4 (C-3); 140.2 (C-3a); 122.9 (C-7a); 86.0 (C-4'); 77.6 (C-1'); 75.2 (C-2'); 72.1 (C-3'); 62.3 (C-5'); 55.6 ($CH_2$).

The corresponding 2'-deoxy derivative is produced in an analogous manner starting with 2'-deoxy-formycin A.

EXAMPLE 2

7-Chloro-3-(2'-deoxyy-$\beta$-D-erythro-pentofuranosyl-)-1H-pyrazolo-[4,3-d]-pyrimidine The compound was synthesized (as described by L. B. Townsend et al., in J. Chem. Soc. (C) 1971, 2443 for the ribofuranosyl derivative) starting from 2'-deoxy-formycin B.

The latter was obtained from commercially available formycin B by Barton deoxygenation (Barton, D. H. R. & Motherwell, W. B. (1981) Pure Appl. Chem. 53, 15).

EXAMPLE 3

7-[1,6-Diaminohexyl]-3-(2'-deoxy-$\beta$-D-erythro-pentofuranosyl)-1H-pyrazolo-[4,3-d]pyrimidine 135 mg (0.5 mmol) Chloro-nucleoside from example 2 is dissolved in 15 ml ethanol, admixed with 300 mg (ca. 2.5 mmol) hexamethylenediamine and refluxed for 3 h.

In the TLC (silica gel; chloroform-methanol 80:20) one a observes an almost quantitative conversion into the title product. The reaction mixture is neutralized with 0.1 M HCl, evaporated and the concentrate is dissolved in 10 ml ethanol. After removing the undissolved components by filtration, it is chromatographed on a silica gel 60 column with a mixture of chloroform methanol (9:1). The combined fractions are evaporated and lyophilized from dioxane (85 mg=48.5% of theory). Elemental analysis for $C_{16}H_{26}N_6O_3$ (350.2); calculated C 54.9,H 7.4, N 24.0; found C 55.3,H 7.6, N 23.7.

EXAMPLE 4

7-[N-Trifluoroacetamidohexyl]-amino-3-(2'-deoxy-$\beta$-D-erythro-pentofuranosyl)-1H-pyrazolo-[4,3-d] pyrimidine 80 mg (0.23 mmol) of the nucleoside from example 3 is dissolved in 10 ml anhydrous pyridine and admixed with 150 μl (ca. 1 mmol) trifluoroacetic acid anhydride. After standing for 5 h at room temperature the acylation is complete according to TLC. The reaction solution is subsequently evaporated in a vacuum and co-evaporated three times with methanol. It is lyophilized from dioxane and 100 mg (98% of theory) of the desired product is obtained.

EXAMPLE 5

7-[N-Trifluoroacetamidohexyl]-amino-3-(2'-deoxy-$\beta$-D-erythro-pentofuranosyl)-1H-pyrazolo-[4,3d] pyrimidine-5'-triphosphate 50 mg (0.11 mmol) of the protected nucleoside from example 4 is converted by phosphorylation with $POCl_3$ into the 5' monophosphate according to the method of Yoshikawa et al. [Tetrahedron Lett. 50, 5065 (1967)]; the desired triphosphate is obtained from this after ion exchange chromatography on DEAE sephadex in a yield of 45 mg (59%) according to the method of Hoard & Ott [J. Am. Chem. Soc. 87, (1965)] by activation with carbonyldiimidazole and reaction with pyrophosphoric acid.

$^{31}$P-NMR (0.1 M EDTA/$D_2O$/$Eth_3N$): −5,4 (d, P-gamma); −10.7 (d, P-alpha); −21.2 (t, P-β).

EXAMPLE 6

Fluorescein-5 (6)-carboxamidohexyl-[7-amino-3-(2'-deoxy-$\beta$-D-erythro-pentofuranosyl)-1H-pyrazolo-[4, 3-d]-pyrimidine-5'-triphosphate]

35 mg (0.05 mmol) of the trifluoroacetyl-protected compound from example 5 is allowed to stand for 1 h at room temperature in 5 ml concentrated ammonia solution and is subsequently evaporated in a vacuum. The residue is taken up in 5 ml 0.1 M borate buffer, pH 8.5 and admixed with a solution of 31 mg (0.065 mmol) 5(6)-carboxy-fluorescein-N-hydroxy-succinimide ester in 5 ml amine-free dimethyl-formamide. It is allowed to stand overnight at room temperature. The reaction mixture is applied to a DEAE sephadex column (30×1 cm) and eluted with a linear LiCl gradient (200 ml each time $H_2O$ to 0.4 M LiCl). 28 mg (59%) of the title substance is obtained after combining the relevant fractions, evaporating, precipitating the concentrate in acetone/ethanol (2:1) and drying.

Spectral data (0.1 M phosphate buffer, pH 9.0): excitation$_{max}$[nm]: 495; emission$_{max}$:[nm]: 521

The digoxigenin-3-O-succinyl-E-aminocaproyl-[7-amino-3-(2'-deoxy-$\beta$-D-erythro-pentofuranosyl)-1H-pyrazolo-[4,3-d]pyrimidine-5'-triphosphate is produced correspondingly by reacting the nucleoside with digoxigenin-3-O-succinyl-aminocaproic acid-N-hydroxy-succinimide ester.

EXAMPLE 7

$N^1$-{8[N-tert.-butoxycarbonyl]-amino-(3,6-dioxa) octyl-1-amidomethyl}-7-amino-3-(2'-deoxy-$\beta$-D-erythro-pentofuranosyl) pyrazolo-[4,3-d]-pyrimidine 125 mg (0.5 mmol) 2'-deoxy-formycin A, 369 mg (1 mmol) ($N^1$-bromoacetamido-$N^8$-t-butoxycarbonyl)-1,8-diamino-3,6-dioxaoctane and 1.4 g $K_2CO_3$ are stirred for 3 h at room temperature in 4 ml methanol/$H_2O$ (1:1). It was processed as described in example 1. 135 mg (50%) of the title compound was obtained after chromatography on a RP-18 column.

EXAMPLE 8

$N^1$-{8-Amino-(3,6-dioxa)octyl-1-amidomethyl}-7-amino-3-(2'-deoxy-$\beta$-D-erythro-pentofuranosyl) pyrazolo-[4,3-d]-pyrimidine-5'-triphosphate 135 mg (0.25 mmol) of the protected nucleoside from example 7 is converted into the triphosphate as described in example 5. After chromatography on RP-18 the Boc protecting group is removed by treating for 1 hour with trifluoroacetic acid. Finally 25 mg of the title compound is obtained after a further chromatography on QAE sephadex.

$^{31}$P-NMR (0.1 M EDTA/D$_2$O/Eth$_3$N): −6.4 (d, P-gamma); −11.1 (d, P-alpha); −21.6 (t, P-β).

EXAMPLE 9

Digoxigenin-3-O-succinyl-E-aminocaproyl-{N$^1$-[8-amino-(3,6-dioxa)octyl-1-amidomethyl]-7-amino-3-(2'-deoxy-β-D-erythro-pentofuranosyl) pyrazolo-[4,3-d]pyrimidine-5'-triphosphate 17 mg (0.024 mmol) of the compound from example 8 is taken up in 5 ml 0.1 M borate buffer, pH 8.5 and admixed with a solution of 25 mg (0.036 mmol) digoxigenin-3-O-succinyl-aminocaproic acid-N-hydroxy-succinimide ester in 5 ml amine-free dimethylformamide. It is allowed to stir for 5 h at room temperature and subsequently chromatographed on RP-18 silica gel. After desalting and lyophilizing 3 mg (ca. 10%) of the labelled triphosphate is obtained.

EXAMPLE 10

4-Oxo-7-(2'-deoxy-β-D-erythro-pentofuranosyl)-3H, 5H-pyrrolo-[3,2-d]pyrimidine

The compound was obtained by Barton deoxygenation from the ribofuranosyl derivative described by M. -I. Lim et al. in Tetrahedron Lett. 1980, 21, 1013.

EXAMPLE 11

4-Chloro-7-(2'-deoxy-β-D-erythro-pentofuranosyl)-3H, 5H-pyrrolo-[3,2-d]pyrimidine The compound was synthesized by halogenation with POCl$_3$ by the method described by Townsend et al., in J. Chem. Soc. (C), 1971, 2443.

EXAMPLE 12

4-[1,6-Diaminohexyl]-7-(2'-deoxy-β-D-erythro-pentofuranosyl)-3H, 5H-pyrrolo-[3,2-d]pyrimidine The derivative was obtained analogous to example 3 starting with the chlorinated compound from example 11 by reaction with diaminohexane.

EXAMPLE 13

Fluorescein-5(6)-carboxamidohexyl-[4-amino-7-(2'-deoxy-β-D-erythro-pentofuranosyl)-3H,5H-pyrrolo-r3,2-d]-pyrimidine-5'-triphosphate]

The title compound was synthesized from the derivative from example 12 via the steps of protecting the diamino function with triflate, preparing the triphosphate and reacting with fluorescein-5(6)-carboxamido-N-hydroxysuccinimide ester. These individual process steps are described in examples 4, 5 and 6.

EXAMPLE 14

5-(2'-Deoxy-β-D-erythro-pentofuranosyl) pyrimidine-2,4-dione-5'-triphosphate 650 mg (2.85 mmol) 5-(2'-deoxy-β-D-erythro-pentofuranosyl)-pyrimidine-2,4-dione prepared according to J. Org. Chem. 1982, 47, 485 by deoxygenation of the commercially available 5-(β-D-erythro-pentofuranosyl)-pyrimidine-2,4-dione (pseudouridine) is converted into the 5'-triphosphate in a one-pot process according to the method of Ludwig [Acta Biochim. et Biophys. Acad. Sci. Hung. (1981), 16, 131]. Anion exchange chromatography on QAE sephadex with a LiCl gradient (water to 0.5 M) and precipitation in acetone/ethanol (2:1) and drying yielded 850 mg (60%) of the title compound.

$^{31}$P-NMR (0.1 M EDTA/D$_2$O/Eth$_3$N): −6.8 (d, P-γ); −11.0 (d, P-α); -22.0 (t, P-β).

EXAMPLE 15

N$^1$-[Ethoxypropionyl]-5-(2'-deoxy-β-D-erythro-pentofuranosyl)pyrimidin-2,4-dione-5'-triphosphate 100 mg (0.2 mmol) of the 2'-deoxy-pseudouridine-5'-triphosphate from example 14 is dissolved in 5 ml 1 M triethylammonium bicarbonate buffer (pH 8.9) and admixed with 5 ml ethanol. 3 ml (ca. 30 mmol) acrylic acid ethyl ester is added and the mixture is stirred for 6.5 h at room temperature. Afterwards it is no longer possible to observe educt according to TLC (i-butyric acid/concentr. ammonia/water=66/1/33). The reaction mixture is evaporated in a vacuum and co-evaporated once with a few ml ethanol and water. The crude product is processed further without further purification as described in example 16.

EXAMPLE 16

N$^1$-[1,3-Diaminopropyl]-5-(2'-deoxy-β-D-erythro-pentofuranosyl)pyrimidin-2,4-dione-5'-triphosphate The product from example 15 is dissolved in 5 ml water and admixed with 5 ml ethanol and 2 ml 1,3 diaminopropane. It is stirred overnight at room temperature and afterwards concentrated with an oil pump in a vacuum until the residue is viscous. It is taken up in a few ml water and the pH is adjusted to 6 with dilute acetic acid. Chromatography/desalting on RP 18 using a triethylammonium acetate/acetonitrile gradient yielded 1000 A$_{260}$ units (ca. 0.1 mmol) of the crude mixture of the compound from which 140 A$_{260}$ units (ca. 20 μmol) of the desired substance was isolated after ion exchange chromatography on QAE sephadex using LiCl.

TLC (i-butyric acid/concentr. ammonia/water=66/1/33): R$_f$ ca. 0.3: positive reaction with ninhydrin.

EXAMPLE 17

N$^1$-Digoxigenin-3-O-methylcarbonyl-ε-aminocaproyl-1,3-diaminopropyl-propionyl]-5-(2'-deoxy-β-D-erythro-pentofuranosyl)pyrimidine-2,4-dione-5'-triphosphate 4.5 mg (5 μmol) of the diaminopropyl derivative from example 16 is dissolved in 1 ml 0.1 M sodium borate buffer, pH 8.5 and 5 mg (7.5 μmol) digoxigenin-3-O-methylcarbonyl-ε-amino-caproic acid-N-hydroxysuccinimide ester dissolved in 1 ml amine-free dimethylformamide is added. The clear solution is allowed to stand for ca. 3 h at room temperature. The reaction solution is afterwards evaporated, the residue is taken up in 1 ml water and purified by means of RP 18 chromatography (column: Inertsil, 250×8 mm, triethylammonium acetate/acetonitrile). After removing the volatile components in a vacuum and lyophilizing one obtains 7 mg (90%) of the title compound.

EXAMPLE 18

Tetramethylrhodamine-5(6)-carboxamido-{N$^1$-[8-N-[3,6-dioxa)octyl-1-amido-methyl]-5-(2'-deoxy-β-D-erythro-pentofuranosyl)pyrimidine-2,4-dione-5'-triphosphate}

The title compound was prepared and purified analogously to example 17 by reacting 18 mg (30 μmol) of the triphosphate from example 16 and from 17 mg (32 μmol) tetramethylrhodamine-5(6)-carboxylic acid-N-hydroxy-succinimide ester in 0.1 M sodium borate buffer, pH 8.5/DMF. 10.5 mg of the TMR-labelled nucleotide was obtained.

Spectral data (0.1 M Na borate buffer, pH 8.5): excitation$_{max}$[nm]: 551: emission$_{max}$:[nm]: 575

EXAMPLE 19

Non-radioactive DNA labelling and detection by incorporation of N$^1$-digoxigenin-3-O-methylcarbonyl-ε-aminocaproyl-1,3-diaminopropyl-propionyl]-5-(2'-deoxy-β-D-erythro-pentofuranosyl) pyrimidine-2,4-dione-5'-triphosphate ]

The DNA labelling and the DNA detection was carried out using the commercially available kit from the Boehringer Mannheim Company (order No. 1093 657). The working instructions describe all required working steps.

For the labelling reaction the dNTP mixture of the kit was substituted by one with N$^1$-[digoxigenin-3-O-methylcarbonyl-ε-aminocaproyl-1,3-diaminopropyl-propionyl]-5-(2'-deoxy-β-D-erythro-pento-furanosyl) pyrimidine-2,4-dione-5'-triphosphate from example 17 (instead of DIG-dUTP).

The immunological detection reaction showed that the incorporation of the compound according to the invention according to example 17 had a detection sensitivity of the labelled DNA which was similar to that when using DIG-dUTP.

Figure 1:
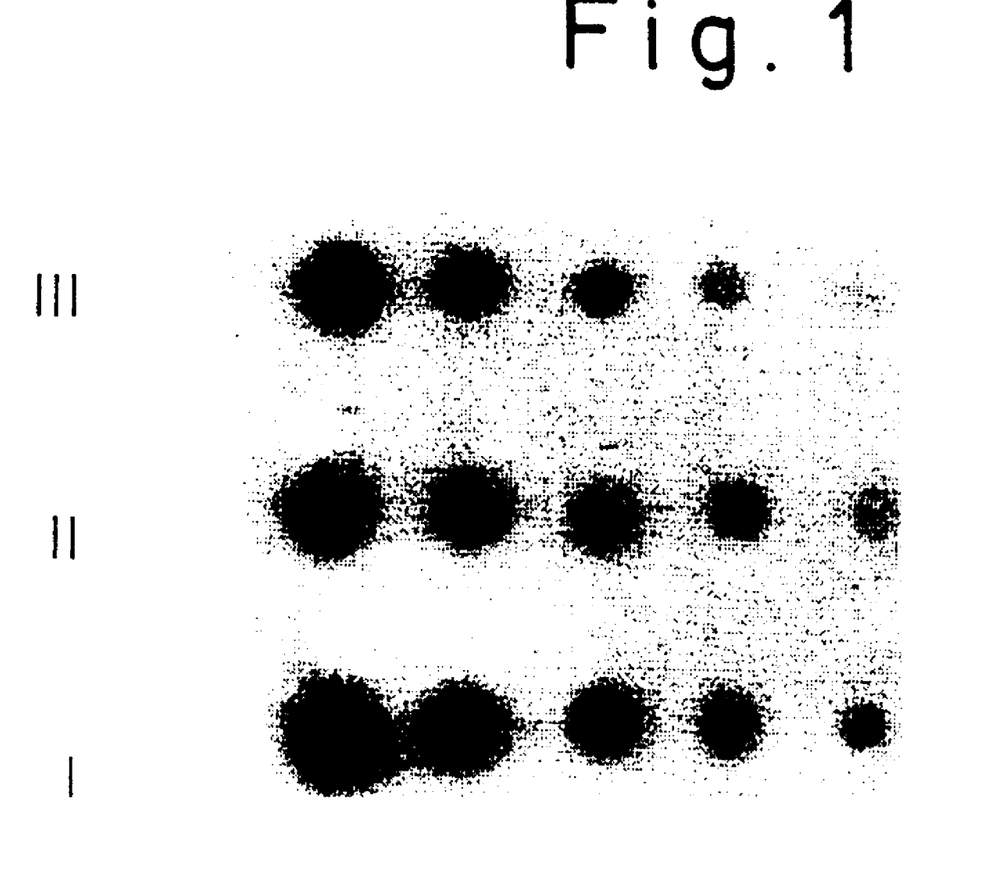

The result which demonstrates the detection and the achieved sensitivity of the system are shown in FIG. 1.

What is claimed is:

1. An oligonucleotide, synthesized from nucleosides, wherein at least one of the nucleosides is a compound of formula V:

wherein $R_1$, $R_2$ and $R_3$ are independently selected from the group consisting of hydrogen, halogen, hydroxy, thio, —(CH$_2$)$_n$—SH wherein n=1–10, —S—(CH$_2$)$_n$CH$_3$ wherein n=0–10, amino, —(CH$_2$)$_n$—NH$_2$ wherein n=1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$—NH$_2$ wherein n=1–6, —C≡C—(CH$_2$)$_n$NH$_2$ wherein n=1–10, carboxy, C$_1$–C$_6$ alkyl, C$_2$–C$_6$ alkenyl, C$_2$–C$_6$ alkynyl, C$_6$H$_5$—, —O—(CH$_2$)$_n$CH$_3$ wherein n=0–6, —O—C$_6$H$_5$, —(CH$_2$)$_n$C$_6$H$_5$ wherein n=1–6, —O—(CH$_2$)$_n$C$_6$H$_5$ wherein n=1–6, and a reporter group, $R_5$ and $R_6$ are independently selected from the group consisting of hydrogen, hydroxy, thio, —(CH$_2$)$_n$—SH wherein n=1–10, —S—(CH$_2$)$_n$CH$_3$ wherein n=0–10, amino, — (CH$_2$)$_n$—NH$_2$ wherein n=1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$—NH$_2$ wherein n=1–6, —C≡C—(CH$_2$)$_n$—NH$_2$ wherein n=1–10, —O—(CH$_2$)$_n$CH$_3$ wherein n=0–6, —O—C$_2$–C$_6$ alkenyl, —O—C$_2$–C$_6$ alkynyl, a protecting group and a reporter group, $R_7$ is a phosphoramidite or H-phosphonate group,

$R_8$ is selected from the group consisting of hydrogen or a hydroxy, thio, —(CH$_2$)$_n$—SH wherein n=1–10, —S—(CH$_2$)$_n$CH$_3$ wherein n=0–10, an amino group, —(CH$_2$)$_n$—NH$_2$ wherein n=1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$—NH$_2$ wherein n=1–6, and —C≡C—(CH$_2$)$_n$—NH$_2$ wherein n=1–10, and $R_9$ is a protecting group, or a tautomer or salt thereof, wherein at least one of $R_1$, $R_2$, $R_3$, $R_5$ and $R_6$ is a reporter group which is bound to the pyrimidine or furanose ring via a linker group, wherein the linker group contains an alkynyl group.

2. An oligonucleotide, synthesized from nucleosides, wherein at least one of the nucleosides is a compound of formula V:

wherein $R_1$, $R_2$ and $R_3$ are independently selected from the group consisting of hydrogen, halogen, hydroxy, thio, —(CH$_2$)$_n$—SH wherein n=1–10, —S—(CH$_2$)$_n$CH$_3$ wherein n=0–10, amino, —(CH$_2$)$_n$—NH$_2$ wherein n=1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$—NH$_2$ wherein n=1–6, —C≡C—(CH$_2$)$_n$—NH$_2$ wherein n=1–10, carboxy, C$_1$–C$_6$ alkyl, C$_2$–C$_6$ alkenyl, C$_2$–C$_6$ alkynyl, C$_6$H$_5$—, —O—(CH$_2$)$_n$CH$_3$ wherein n=0–6, —O—C$_6$H$_5$, —(CH$_2$)$_n$C$_6$H$_5$ wherein n=1–6, —O—(CH$_2$)$_n$C$_6$H$_5$ wherein n=1–6, and a reporter group, $R_5$ and $R_6$ are independently selected from the group consisting of hydrogen, hydroxy, thio, —(CH$_2$)$_n$—SH wherein n=1–10, —S—(CH$_2$)$_n$CH$_3$ wherein n=0–10, amino, —(CH$_2$)$_n$—NH$_2$ wherein n=1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$—NH$_2$ wherein n=1–6, —C≡C—(CH$_2$)$_n$—NH$_2$ wherein n=1–10, —O—(CH$_2$)$_n$CH$_3$ wherein n=0–6, —O—C$_2$–C$_6$ alkenyl, —O—C$_2$–C$_6$ alkynyl, a protecting group and a reporter group, $R_7$ is a phosphoramidite or H-phosphonate group, $R_8$ is selected from the group consisting of hydrogen or a hydroxy, thio, —(CH$_2$)$_n$—SH wherein n=1–10, —S—

$(CH_2)_nCH_3$ wherein n=0–10, an amino group, $-(CH_2)_n-NH_2$ wherein n=1–15, $-(CH_2)_nC(=O)-NH_2$ wherein n=1–15, $-NH-(CH_2)_nCH_3$ wherein n=0–15, $-NH-(CH_2)_nNH_2$ wherein n=1–15, $-CH=(CH_2)_n-NH_2$ wherein n=1–6, and $C\equiv C-(CH_2)_n-NH_2$ wherein n=1–10, and $R_9$ is a protecting group, or a tautomer or salt thereof, wherein at least one of $R_1$, $R_2$, $R_3$, $R_5$ and $R_6$ is a reporter group which is bound to the pyrimidine or furanose ring via a linker group, wherein the linker group contains an ethylene glycol group.

3. An oligonucleotide, synthesized from nucleosides, wherein at least one of the nucleosides is a compound of formula V:

wherein $R_1$, $R_2$ and $R_3$ are independently selected from the group consisting of hydrogen, halogen, hydroxy, thio, $-(CH_2)_n-SH$ wherein n=1–10, $-S-(CH_2)_nCH_3$ wherein n=0–10, amino, $-(CH_2)_n-NH_2$ wherein n=1–15, $-(CH_2)_nC(=O)-NH_2$ wherein n=1–1–15, $-NH-(CH_2)_nCH_3$ wherein n=0–15, $-NH-(CH_2)_nNH_2$ wherein n=1–15, $-CH=(CH_2)_n-NH_2$ wherein n=1–6, $-C\equiv C-(CH_2)_n-NH_2$ wherein n=1–10, carboxy, $C_1$-$C_6$ alkyl, $C_2$-$C_6$ alkenyl, $C_2$-$C_6$ alkynyl, $C_6H_5-$, $-O-(CH_2)_nCH_3$ wherein n=0–6, $-O-C_6H_5$, $-(CH_2)_nC_6H_5$ wherein n=1–6, $-O-(CH_2)_nC_6H_5$ wherein n=1–6, and a reporter group, $R_5$ and $R_6$ are independently selected from the group consisting of hydrogen, hydroxy, thio, $-(CH_2)_n-SH$ wherein n=1–10, $-S-(CH_2)_nCH_3$ wherein n=0–10, amino, $-(CH_2)_n-NH_2$ wherein n=1–15, $-(CH_2)_nC(=O)-NH_2$ wherein n=1–15, $-NH-(CH_2)_nCH_3$ wherein n=0–15, $-NH-(CH_2)_nNH_2$ wherein n=1–15, $-CH=(CH_2)_n-NH_2$ wherein n=1–6, $-C\equiv C-(CH_2)_n-NH_2$ wherein n=1–10, $-O-(CH_2)_nCH_3$ wherein n=0–6, $-O-C_2$-$C_6$ alkenyl, $-O-C_2$-$C_6$ alkynyl, a protecting group and a reporter group, $R_7$ is a phosphoramidite or H-phosphonate group,

$R_8$ is selected from the group consisting of hydrogen or a hydroxy, thio, $-(CH_2)_n-SH$ wherein n=1–10, $-S-(CH_2)_nCH_3$ wherein n=0–10, an amino group, $-(CH_2)_n-NH_2$ wherein n=1–15, $-(CH_2)_nC(=O)-NH_2$ wherein n=1–15, $-NH-(CH_2)_nCH_3$ wherein n=0–15, $-NH-(CH_2)_nNH_2$ wherein n=1–15, $-CH=(CH_2)_n-NH_2$ wherein n=1–6, and $-C\equiv C-(CH_2)_n-NH_2$ wherein n=1–10, and $R_9$ is a protecting group, or a tautomer or salt thereof, wherein at least one of $R_1$, $R_2$, $R_3$, $R_5$ and $R_6$ is a reporter group which is bound to the pyrimidine or furanose ring via a linker group.

4. An oligonucleotide, synthesized from nucleosides, wherein at least one of the nucleosides is a compound of formula V:

wherein $R_1$, $R_2$ and $R_3$ are independently selected from the group consisting of hydrogen, halogen, hydroxy, thio, $-(CH_2)_n-SH$ wherein n=1–10, $-S-(CH_2)_nCH_3$ wherein n=0–10, amino, $-(CH_2)_n-NH_2$ wherein n=1–15, $-(CH_2)_nC(=O)-NH_2$ wherein n=1–15, $-NH-(CH_2)_nCH_3$ wherein n=0–15, $-NH-(CH_2)_nNH_2$ wherein n=1–15, $-CH=(CH_2)_n-NH_2$ wherein n=1–6, $-C\equiv C-(CH_2)_n-NH_2$ wherein n=1–10, carboxy, $C_1$-$C_6$ alkyl, $C_2$-$C_6$ alkenyl, $C_2$-$C_6$ alkynyl, $C_6H_5-$, $-O-(CH_2)_nCH_3$ wherein n=0–6, $-O-C_6H_5$, $-(CH_2)_nC_6H_5$ wherein n=1–6, $-O-(CH_2)_nC_6H_5$ wherein n=1–6, and a reporter group, $R_5$ and $R_6$ are independently selected from the group consisting of hydrogen, hydroxy, thio, $-(CH_2)_n-SH$ wherein n=1–10, $-S-(CH_2)_nCH_3$ wherein n=0–10, amino, $-(CH_2)_n-NH_2$ wherein n=1–15, $-(CH_2)_nC(=O)-NH_2$ wherein n=1–15, $-NH-(CH_2)_nCH_3$ wherein n=0–15, $-NH-(CH_2)_nNH_2$ wherein n=1–15, $-CH=(CH_2)_n-NH_2$ wherein n=1–6, $-C\equiv C-(CH_2)_n-NH_2$ wherein n=1–10, $-O-(CH_2)_nCH_3$ wherein n=0–6, $-O-C_2$-$C_6$ alkenyl, $-O-C_2$-$C_6$ alkynyl, a protecting group and a reporter group, $R_7$ is a phosphoramidite or H-phosphonate group,

$R_8$ is selected from the group consisting of hydrogen or a hydroxy, thio, $-(CH_2)_n-SH$ wherein n=1–10, $-S-(CH_2)_nCH_3$ wherein n=0–10, an amino group, $-(CH_2)_n-NH_2$ wherein n=1–15, $-(CH_2)_nC(=O)-NH_2$ wherein n=1–15, $-NH-(CH_2)_nCH_3$ wherein n=0–15, $-NH-(CH_2)_nNH_2$ wherein n=1–15, $-CH=(CH_2)_n-NH_2$ wherein n=1–6, and $-C\equiv C-(CH_2)_n-NH_2$ wherein n=1–10, and $R_9$ is a protecting group, or a tautomer or salt thereof, wherein at least one of $R_1$, $R_2$, $R_3$, $R_5$ and $R_6$ is a reporter group which is bound to the pyrimidine or furanose ring via a linker group, wherein the linker group contains an alkynyl group and is of a sufficient length such that the compound can be incorporated into the oligonucleotide by means of a polymerase.

5. An oligonucleotide, synthesized from nucleosides, wherein at least one of the nucleosides is a compound of formula V:

wherein

R$_1$, R$_2$ and R$_3$ are independently selected from the group consisting of hydrogen, halogen, hydroxy, thio, —(CH$_2$)$_n$—SH wherein n=1–10, —S—(CH$_2$)$_n$CH$_3$ wherein n=0–10, amino, —(CH$_2$)$_n$—NH$_2$ wherein n=1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$—NH$_2$ wherein n=1–6, —C≡C—(CH$_2$)$_n$—NH$_2$ wherein n=1–10, carboxy, C$_1$-C$_6$ alkyl, C$_2$-C$_6$ alkenyl, C$_2$-C$_6$ alkinyl, C$_6$H$_5$—, —O—(CH$_2$)$_n$CH$_3$ wherein n=0–6, —O—C$_6$H$_5$, —(CH$_2$)$_n$C$_6$H$_5$ wherein n=1–6, —O—(CH$_2$)$_n$C$_6$H$_5$ wherein n=1–6, and a reporter group, R$_5$ and R$_6$ are independently selected from the group consisting of hydrogen, hydroxy, thio, —(CH$_2$)$_n$—SH wherein n=1–10, —S—(CH$_2$)$_n$CH$_3$ wherein n=0–10, amino, —(CH$_2$)$_n$—NH$_2$ wherein n=1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$—NH$_2$ wherein n=1–6, —C≡C—(CH$_2$)$_n$—NH$_2$ wherein n=1–10, —O—(CH$_2$)$_n$CH$_3$ wherein n=0–6, —O—C$_2$-C$_6$ alkenyl, —O—C$_2$-C$_6$ alkinyl, a protecting group and a reporter group, R$_7$ is a phosphoramidite or H-phosphonate group, R$_8$ is selected from the group consisting of hydrogen or a hydroxy, thio, —(CH$_2$)$_n$—SH wherein n=1–10, —S—(CH$_2$)$_n$CH$_3$ wherein n=0–10, an amino group, —(CH$_2$)$_n$—NH$_2$ wherein n=1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$—NH$_2$ wherein n=1–6, and —C≡C—(CH$_2$)$_n$—NH$_2$ wherein n=1–10, and R$_9$ is a protecting group, or a tautomer or salt thereof, wherein at least one of R$_1$, R$_2$, R$_3$, R$_5$ and R$_6$ is a reporter group which is bound to the pyrimidine or furanose ring via a linker group, wherein the linker group contains an ethylene glycol group and is of a sufficient length such that the compound can be incorporated into the oligonucleotide by means of a polymerase.

6. The oligonucleotide of claim 1, wherein the reporter group is a detectable group.

7. The oligonucleotide of claim 2, wherein the reporter group is a detectable group.

8. The oligonucleotide of claim 3, wherein the reporter group is a detectable group.

9. The oligonucleotide of claim 4, wherein the reporter group is a detectable group.

10. The oligonucleotide of claim 5, wherein the reporter group is a detectable group.

11. The oligonucleotide of claim 6, wherein the detectable group is selected from the group consisting of a hapten, a fluorophore, a metal chelating group, a lumiphore, a protein and an intercalator.

12. The oligonucleotide of claim 7, wherein the detectable group is selected from the group consisting of a hapten, a fluorophore, a metal chelating group, a lumiphore, a protein and an intercalator.

13. The oligonucleotide of claim 8, wherein the detectable group is selected from the group consisting of a hapten, a fluorophore, a metal chelating group, a lumiphore, a protein and an intercalator.

14. The oligonucleotide of claim 9, wherein the detectable group is selected from the group consisting of a hapten, a fluorophore, a metal chelating group, a lumiphore, a protein and an intercalator.

15. The oligonucleotide of claim 10, wherein the detectable group is selected from the group consisting of a hapten, a fluorophore, a metal chelating group, a lumiphore, a protein and an intercalator.

16. A nucleic acid, synthesized from nucleosides, wherein at least one of the nucleosides is a compound of formula V:

wherein

R$_1$, R$_2$ and R$_3$ are independently selected from the group consisting of hydrogen, halogen, hydroxy, thio, —(CH$_2$)$_n$—SH wherein n=1–10, —S—(CH$_2$)$_n$CH$_3$ wherein n=0–10, amino, —(CH$_2$)$_n$—NH$_2$ wherein n=1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$—NH$_2$ wherein n=1–6, C≡C—(CH$_2$)$_n$—NH$_2$ wherein n=1–10, carboxy, C$_1$-C$_6$ alkyl, C$_2$-C$_6$ alkenyl, C$_2$-C$_6$ alkinyl, C$_6$H$_5$—, —O—(CH$_2$)$_n$CH$_3$ wherein n=0–6, —O—C$_6$H$_5$, —(CH$_2$)$_n$C$_6$H$_5$ wherein n=1–6, —O—(CH$_2$)$_n$C$_6$H$_5$ wherein n=1–6, and a reporter group, R$_5$ and R$_6$ are independently selected from the group consisting of hydrogen, hydroxy, thio, —(CH$_2$)$_n$—SH wherein n=1–10, —S—(CH$_2$)$_n$CH$_3$ wherein n=0–10, amino, —(CH$_2$)$_n$—NH$_2$ wherein n1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$—NH$_2$ wherein n=1–6, —C≡C—(CH$_2$)$_n$—NH$_2$ wherein n=1–10, —O—(CH$_2$)$_n$CH$_3$ wherein n=0–6, —O—C$_2$-C$_6$ alkenyl, —O—C$_2$-C$_6$ alkynyl, a protecting group and a reporter group, R$_7$ is a phosphoramidite or H-phosphonate group,

R$_8$ is selected from the group consisting of hydrogen or a hydroxy, thio, —(CH$_2$)$_n$—SH wherein n=1–10, —S—(CH$_2$)$_n$CH$_3$ wherein n=0–10, an amino group, —(CH$_2$)$_n$—NH$_2$ wherein n=1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$—NH$_2$ wherein n=1–6, (CH$_2$)$_n$—NH$_2$ wherein n=1–10, and R$_9$ is a protecting group, or a tautomer or salt thereof, wherein at least one of R$_1$, R$_2$, R$_3$, R$_5$ and R$_6$ is a reporter group which is bound to the pyrimidine or furanose ring via a linker group, wherein the linker group contains an alkynyl group.

17. A nucleic acid, synthesized from nucleosides, wherein at least one of the nucleosides is a compound of formula V:

wherein $R_1$, $R_2$ and $R_3$ are independently selected from the group consisting of hydrogen, halogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, carboxy, $C_1$-$C_6$ alkyl, $C_2$-$C_6$ alkenyl, $C_2$-$C_6$ alkynyl, $C_6H_5$—, —O—$(CH_2)_n CH_3$ wherein n=0–6, —O—$C_6H_5$, —$(CH_2)_n C_6H_5$ wherein n=1–6, —O—$(CH_2)_n C_6H_5$ wherein n=1–6, and a reporter group, $R_5$ and $R_6$ are independently selected from the group consisting of hydrogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, —O—$(CH_2)_n CH_3$ wherein n=0–6, —O—$C_2$-$C_6$ alkenyl, —O—$C_2$-$C_6$ alkynyl, a protecting group and a reporter group, $R_7$ is a phosphoramidite or H-phosphonate group,

$R_8$ is selected from the group consisting of hydrogen or a hydroxy, thio, —$(CH_2)_n$—SH wherein n=1–10, —S—$(CH_2)_n CH_3$ wherein n=0–10, an amino group, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, and —C≡C—$(CH_2)_n$—$NH_2$ wherein n=1–10, and $R_9$ is a protecting group, or a tautomer or salt thereof, wherein at least one of $R_1$, $R_2$, $R_3$, $R_5$ and $R_6$ is a reporter group which is bound to the pyrimidine or furanose ring via a linker group, wherein the linker group contains an ethylene glycol group.

18. A nucleic acid, synthesized from nucleosides, wherein at least one of the nucleosides is a compound of formula V:

wherein $R_1$, $R_2$ and $R_3$ are independently selected from the group consisting of hydrogen, halogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, carboxy, $C_1$-$C_6$ alkyl, $C_2$-$C_6$ alkenyl, $C_2$-$C_6$ alkynyl, $C_6H_5$—, —O—$(CH_2)_n CH_3$ wherein n=0–6, —O—$C_6H_5$, —$(CH_2)_n C_6H_5$ wherein n=1–6, —O—$(CH_2)_n C_6H_5$ wherein n=1–6, and a reporter group, $R_5$ and $R_6$ are independently selected from the group consisting of hydrogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, —O—$(CH_2)_n CH_3$ wherein n=0–6, —O—$C_2$-$C_6$ —O—$C_2$-$C_6$ alkynyl, a protecting group and a reporter group, $R_7$ is a phosphoramidite or H-phosphonate group,

$R_8$ is selected from the group consisting of hydrogen or a hydroxy, thio, —$(CH_2)_n$—SH wherein n=1–10, —S—$(CH_2)_n CH_3$ wherein n=0–10, an amino group, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, and —C≡C—$(CH_2)_n$—$NH_2$ wherein n=1–10, and $R_9$ is a protecting group, or a tautomer or salt thereof, wherein at least one of $R_1$, $R_2$, $R_3$, $R_5$ and $R_6$ is a reporter group which is bound to the pyrimidine or furanose ring via a linker group.

19. A nucleic acid, synthesized from nucleosides, wherein at least one of the nucleosides is a compound of formula V:

wherein
$R_1$, $R_2$ and $R_3$ are independently selected from the group consisting of hydrogen, halogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, carboxy, $C_1$–$C_6$ alkyl, $C_2$–$C_6$ alkenyl, $C_2$–$C_6$ alkenyl, $C_6H_5$—, —O—$(CH_2)_n CH_3$ wherein n=0–6, —O—$C_6H_5$, —$(CH_2)_n C_6H_5$ wherein n=1–6, —O—$(CH_2)_n C_6H_5$ wherein n=1–6, and a reporter group, $R_5$ and $R_6$ are independently selected from the group consisting of hydrogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, —O—$(CH_2)_n CH_3$ wherein n=0–6, —O—$C_2$-$C_6$ alkenyl, —O—$C_2$-$C_6$ alkinyl, a protecting group and a reporter group, $R_7$ is a phosphoramidite or H-phosphonate group,

$R_8$ is selected from the group consisting of hydrogen or a hydroxy, thio, —$(CH_2)_n$—SH wherein n=1–10, —S—$(CH_2)_n CH_3$ wherein n=1–10, an amino group, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, and —C≡C—$(CH_2)_n$—$NH_2$ wherein n=1–10, and $R_9$ is a protecting group, or a tautomer or salt thereof, wherein at least one of $R_1$, $R_2$, $R_3$, $R_5$ and $R_6$ is a reporter group which is bound to the pyrimidine or furanose ring via a linker group, wherein the linker group contains an alkynyl group and is of a sufficient length such that the compound can be incorporated into the nucleic acid by means of a polymerase.

20. A nucleic acid, synthesized from nucleosides, wherein at least one of the nucleosides is a compound of formula V:

wherein
$R_1$, $R_2$ and $R_3$ are independently selected from the group consisting of hydrogen, halogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n$ $NH_2$ wherein n=1–15, —CH=$(CH_2)_n$—$NH_2$ wherein n=1–6, —C≡C—$(CH_2)_n$—$NH_2$ wherein n=1–10, carboxy, $C_1$–$C_6$ alkyl, $C_2$–$C_6$ alkenyl, $C_2$–$C_6$ alkinyl, $C_6H_5$—, —O—$(CH_2)_n CH_3$ wherein n=0–6, —O—$C_6H_5$, —$(CH_2)_n C_6H_5$ wherein n=1–6, —O—$(CH_2)_n C_6H_5$ wherein n=1–6, and a reporter group, $R_5$ and $R_6$ are independently selected from the group consisting of hydrogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, —O—$(CH_2)_n CH_3$ wherein n=0–6, —O—$C_2$-$C_6$ alkenyl, —O—$C_2$-$C_6$ alkinyl, a protecting group and a reporter group, $R_7$ is a phosphoramidite or H-phosphonate group, $R_8$ is selected from the group consisting of hydrogen or a hydroxy, thio, —$(CH_2)_n$—SH wherein n=1–10, —S—$(CH_2)_n CH_3$ wherein n=1–10, an amino group, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, and —C≡C—$(CH_2)_n$—$NH_2$ wherein n=1–10, and $R_9$ is a protecting group, or a tautomer or salt thereof, wherein at least one of $R_1$, $R_2$, $R_3$, $R_5$ and $R_6$ is a reporter group which is bound to the pyrimidine or furanose ring via a linker group, wherein the linker group contains an ethylene glycol group and is of a sufficient length such that the compound can be incorporated into the nucleic acid by means of a polymerase.

21. The nucleic acid of claim 16, wherein the reporter group is a detectable group.

22. The nucleic acid of claim 17, wherein the reporter group is a detectable group.

23. The nucleic acid of claim 18, wherein the reporter group is a detectable group.

24. The nucleic acid of claim 19, wherein the reporter group is a detectable group.

25. The nucleic acid of claim 20, wherein the reporter group is a detectable group.

26. The nucleic acid of claim 21, wherein the detectable group is selected from the group consisting of a hapten, a fluorophore, a metal chelating group, a lumiphore, a protein and an intercalator.

27. The nucleic acid of claim 22, wherein the detectable group is selected from the group consisting of a hapten, a fluorophore, a metal chelating group, a lumiphore, a protein and an intercalator.

28. The nucleic acid of claim 23, wherein the detectable group is selected from the group consisting of a hapten, a fluorophore, a metal chelating group, a lumiphore, a protein and an intercalator.

29. The nucleic acid of claim 24, wherein the detectable group is selected from the group consisting of a hapten, a fluorophore, a metal chelating group, a lumiphore, a protein and an intercalator.

30. The nucleic acid of claim 25, wherein the detectable group is selected from the group consisting of a hapten, a fluorophore, a metal chelating group, a lumiphore, a protein and an intercalator.

31. A method for detecting nucleic acids, comprising
(a) hybridizing a nucleic acid to be detected with a labeled probe, wherein said probe is synthesized from nucleosides, wherein at least one of the nucleosides is a compound of formula V:

wherein

R₁, R₂ and R₃ are independently selected from the group consisting of hydrogen, halogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, carboxy, $C_1$–$C_6$ alkyl, $C_2$–$C_6$ alkenyl, $C_2$–$C_6$ alkynyl, $C_6H_5$—, —O—$(CH_2)_n CH_3$ wherein n=0–6, —O—$C_6H_5$, —$(CH_2)_n C_6H_5$ wherein n=1–6, —O—$(CH_2)_n C_6H_5$ wherein n=1–6, and a label, R₅ and R₆ are independently selected from the group consisting of hydrogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, —O—$(CH_2)_n CH_3$ wherein n=0–6, —O—$C_2$–$C_6$ —O—$C_2$–$C_6$ alkynyl, a protecting group and a label, R₇ is a phosphoramidite or H-phosphonate group, R₈ is selected from the group consisting of hydrogen or a hydroxy, thio, —$(CH_2)_n$—SH wherein n=1–10, —S—$(CH_2)_n CH_3$ wherein n=0–10, an amino group, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, and —C≡C—$(CH_2)_n$—$NH_2$ wherein n=1–10, and R₉ is a protecting group, or a tautomer or salt thereof, wherein at least one of R₁, R₂, R₃, R₅ and R₆ is a label which is bound to the pyrimidine or furanose ring via a linker group, wherein the linker group contains an alkynyl group, and (b) detecting said labeled probe as an indication of the presence of said nucleic acid to be detected.

32. A method for detecting nucleic acids, comprising (a) hybridizing a nucleic acid to be detected with a labeled probe, wherein said probe is synthesized from nucleosides, wherein at least one of the nucleosides is a compound of formula V:

wherein

R₁, R₂ and R₃ are independently selected from the group consisting of hydrogen, halogen, hydroxy, thio, —$(CH_2)_n$—SH wherein n=1–10, —S—$(CH_2)_n CH_3$ wherein n=0–10, amino, —$(CH_2)_n NH_2$ wherein n=1–15, —$(CH_2)$—$C(=O)$—$NH_2$ wherein n=1–5, —NH—$(CH_2)_n CH_3$ wherein n=0–5, —NH—$(CH_2)_n NH_2$ wherein n=1–15, —CH=$(CH_2)_n$—$NH_2$ wherein n=1–6, —C≡C—$(CH_2)_n NH_2$ wherein n=1–10, carboxy, $C_1$–$C_6$ alkyl, $C_2$–$C_6$ alkenyl, $C_2$–$C_6$ alkynyl, $C_6H_5$—, —O—$(CH_2)_n CH_3$ wherein n=0–6, —O—$C_6H_5$, —$(CH_2)_n C_6H_5$ wherein n=1–6, —O—$(CH_2)_n C_6H_5$ wherein n=1–6, and a label, R₅ and R₆ are independently selected from the group consisting of hydrogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n NH_2$ wherein n=1–10, —O—$(CH_2)_n CH_3$ wherein n=0–6, —O—$C_2$–$C_6$ alkenyl, —O—$C_2$–$C_6$ alkynyl, a protecting group and a label, R₇ is a phosphoramidite or H-phosphonate group, R₈ is selected from the group consisting of hydrogen or a hydroxy, thio, —$(CH_2)_n$—SH wherein n=1–10, —S—$(CH_2)_n CH_3$ wherein n=0–10, an amino group, —$(CH_2)_n$—$NH_2$ wherein n=1–15, —$(CH_2)_n C(=O)$—$NH_2$ wherein n=1–15, —NH—$(CH_2)_n$—$CH_3$ wherein n=0–15, —NH—$(CH_2)_n NH_2$ wherein n=1–15, —CH=$(CH_2)_n$—$NH_2$ wherein n=1–6, and —C≡C—$(CH_2)_n$—$NH_2$ wherein n=1–10, and R₉ is a protecting group, or a tautomer or salt thereof, wherein at least one of R₁, R₂, R₃, R₅ and R₆ is a label which is bound to the pyrimidine or furanose ring via a linker group, wherein the linker group contains an ethylene glycol group, and (b) detecting said labeled probe as an indication of the presence of said nucleic acid to be detected.

33. A method for detecting nucleic acids, comprising (a) hybridizing a nucleic acid to be detected with a labeled probe, wherein said probe is synthesized from nucleosides, wherein at least one of the nucleosides is a compound of formula V:

wherein $R_1$, $R_2$ and $R_3$ are independently selected from the group consisting of hydrogen, halogen, hydroxy, thio, —$(CH_2)_n$—SH wherein n=1–10, —S—$(CH_2)_n CH_3$ wherein n=0–10, amino, —$(CH_2)_n NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, carboxy, $C_1$-$C_6$ alkyl, $C_2$-$C_6$ alkenyl, $C_2$-$C_6$ alkynyl, $C_6H_5$—, —O—$(CH_2)_n CH_3$ wherein n=0–6, —O—$C_6H_5$, —$(CH_2)_n C_6H_5$ wherein n=1–6, —O—$(CH_2)_n C_6H_5$ wherein n=1–6, and a label, $R_5$ and $R_6$ are independently selected from the group consisting of hydrogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n NH_2$ wherein n=1–6, —C≡C—$(CH_2)_n$—$NH_2$ wherein n=1–10, —O—$(CH_2)_n CH_3$ wherein n=0–6, —O—$C_2$-$C_6$ alkenyl, —O—$C_2$-$C_6$ alkynyl, a protecting group and a label, $R_7$ is a phosphoramidite or H-phosphonate group, $R_8$ is selected from the group consisting of hydrogen or a hydroxy, thio, —$(CH_2)_n$—SH wherein n=1–10, —S—$(CH_2)_n CH_3$ wherein n=0–10, an amino group, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, and —C≡C—$(CH_2)_n$—$NH_2$ wherein n=1–10, and $R_9$ is a protecting group, or a tautomer or salt thereof, wherein at least one of $R_1$, $R_2$, $R_3$, $R_5$ and $R_6$ is a label which is bound to the pyrimidine or furanose ring via a linker group, and (b) detecting said labeled probe as an indication of the presence of said nucleic acid to be detected.

34. A method for detecting nucleic acids, comprising (a) hybridizing a nucleic acid to be detected with a labeled probe, wherein said probe is synthesized from nucleosides, wherein at least one of the nucleosides is a compound of formula V:

wherein $R_1$, $R_2$ and $R_3$ are independently selected from the group consisting of hydrogen, halogen, hydroxy, thio, —$(CH_2)_n$—SH wherein n=1–10, —S—$(CH_2)_n CH_3$ wherein n=0–10, amino, —$(CH_2)_n NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n NH_2$ wherein n=1–10, carboxy, $C_1$-$C_6$ alkyl, $C_2$-$C_6$ alkenyl, $C_2$-$C_6$ alkynyl, $C_6H_5$—, —O—$(CH_2)_n CH_3$ wherein n=0–6, —O—$C_6H_5$, —$(CH_2)_n C_6H_5$ wherein n=1–6, —O—$(CH_2)_n C_6H_5$ wherein n=1–6, and a label, $R_5$ and $R_6$ are independently selected from the group consisting of hydrogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, —O—$(CH_2)_n CH_3$ wherein n=0–6, —O—$C_2$-$C_6$ alkenyl, —O—$C_2$-$C_6$ alkynyl, a protecting group and a label, $R_7$ is a phosphoramidite or H-phosphonate group, $R_8$ is selected from the group consisting of hydrogen or a hydroxy, thio, —$(CH_2)_n$—SH wherein n=1–10, —S—$(CH_2)_n CH_3$ wherein n=0–10, an amino group, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, and —C≡C—$(CH_2)_n$—$NH_2$ wherein n=1–10, and $R_9$ is a protecting group, or a tautomer or salt thereof, wherein at least one of $R_1$, $R_2$, $R_3$, $R_5$ and $R_6$ is a label which is bound to the pyrimidine or furanose ring via a linker group, wherein the linker group contains an alkynyl group and is of a sufficient length such that the compound can be incorporated into the probe by means of a polymerase, and (b) detecting said labeled probe as an indication of the presence of said nucleic acid to be detected.

35. A method for detecting nucleic acids, comprising (a) hybridizing a nucleic acid to be detected with a labeled probe, wherein said probe is synthesized from nucleosides, wherein at least one of the nucleosides is a compound of formula V:

wherein

R$_1$, R$_2$ and R$_3$ are independently selected from the group consisting of hydrogen, halogen, hydroxy, thio, —(CH$_2$)$_n$—SH wherein n=1–10, —S—(CH$_2$)$_n$CH$_3$ wherein n=0–10, amino, —(CH$_2$)$_n$—NH$_2$ wherein n=1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$—NH$_2$ wherein n=1–6, —C≡C—(CH$_2$)$_n$—NH$_2$ wherein n=1–10, carboxy, C$_1$–C$_6$ alkyl, C$_2$–C$_6$ alkenyl, C$_2$–C$_6$ alkynyl, C$_6$H$_5$—, —O—(CH$_2$)$_n$CH$_3$ wherein n=0–6, —O—C$_6$H$_5$ wherein n=1–6, —O—(CH$_2$)$_n$C$_6$H$_5$ wherein n=1–6, and a label, R$_5$ and R$_6$ are independently selected from the group consisting of hydrogen, hydroxy, thio, —(CH$_2$)$_n$—SH wherein n=1–10, —S—(CH$_2$)$_n$CH$_3$ wherein n=0–10, amino, —(CH$_2$)$_n$—NH$_2$ wherein n=1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$NH$_2$ wherein n=1–6, —C≡C—(CH$_2$)$_n$—NH$_2$ wherein n=1–10, —O—(CH$_2$)$_n$CH$_3$ wherein n=0–6, —O—C$_2$–C$_6$ alkenyl, —O—C$_2$–C$_6$ alkynyl, a protecting group and a label, R$_7$ is a phosphoramidite or H-phosphonate group, R$_8$ is selected from the group consisting of hydrogen or a hydroxy, thio, —(CH$_2$)$_n$—SH wherein n=1–10, —S—(CH$_2$)$_n$CH$_3$ wherein n=0–10, an amino group, —(CH$_2$)$_n$—NH$_2$ wherein n=1–15, —(CH$_2$)$_n$C(=O)—NH$_2$ wherein n=1–15, —NH—(CH$_2$)$_n$CH$_3$ wherein n=0–15, —NH—(CH$_2$)$_n$NH$_2$ wherein n=1–15, —CH=(CH$_2$)$_n$—NH$_2$ wherein n=1–6, and —C≡C—(CH$_2$)$_n$—NH$_2$ wherein n=1–10, and R$_9$ is a protecting group, or a tautomer or salt thereof, wherein at least one of R$_1$, R$_2$, R$_3$, R$_5$ and R$_6$ is a label which is bound to the pyrimidine or furanose ring via a linker group, wherein the linker group contains an ethylene glycol group and is of a sufficient length such that the compound can be incorporated into the probe by means of a polymerase, and (b) detecting said labeled probe as an indication of the presence of said nucleic acid to be detected.

36. A method for sequencing a DNA sequence, comprising (a) providing a plurality of oligonucleotides according to claim 1, wherein the reporter group is a detectable group, each of the plurality of oligonucleotides beginning at a fixed location on the DNA sequence and randomly terminating at different residues on the DNA sequence, and (b) determining the length and termination residue of the plurality of oligonucleotides as an indication of the DNA sequence.

37. A method for sequencing a DNA sequence, comprising (a) providing a plurality of oligonucleotides according to claim 2, wherein the reporter group is a detectable group, each of the plurality of oligonucleotides beginning at a fixed location on the DNA sequence and randomly terminating at different residues on the DNA sequence, and (b) determining the length and termination residue of the plurality of oligonucleotides as an indication of the DNA sequence.

38. A method for sequencing a DNA sequence, comprising (a) providing a plurality of oligonucleotides according to claim 3, wherein the reporter group is a detectable group, each of the plurality of oligonucleotides beginning at a fixed location on the DNA sequence and randomly terminating at different residues on the DNA sequence, and (b) determining the length and termination residue of the plurality of oligonucleotides as an indication of the DNA sequence.

39. A method for sequencing a DNA sequence, comprising (a) providing a plurality of oligonucleotides according to claim 4, wherein the reporter group is a detectable group, each of the plurality of oligonucleotides beginning at a fixed location on the DNA sequence and randomly terminating at different residues on the DNA sequence, and (b) determining the length and termination residue of the plurality of oligonucleotides as an indication of the DNA sequence.

40. A method for sequencing a DNA sequence, comprising (a) providing a plurality of oligonucleotides according to claim 5, wherein the reporter group is a detectable group, each of the plurality of oligonucleotides beginning at a fixed location on the DNA sequence and randomly terminating at different residues on the DNA sequence, and (b) detecting the detectable groups and correlating the detection with the length and termination residue of the plurality of oligonucleotides as an indication of the DNA sequence.

41. A method for in situ hybridization, comprising (a) immobilizing a nucleic acid on a solid support to produce an immobilized nucleic acid, (b) hybridizing a nucleic acid according to claim 16 with said immobilized nucleic acid, wherein the reporter group is a detectable group, and (c) detecting the detectable group as an indication of the presence of said immobilized nucleic acid.

42. A method for in situ hybridization, comprising (a) immobilizing a nucleic acid on a solid support to produce an immobilized nucleic acid, (b) hybridizing a nucleic acid according to claim 17 with said immobilized nucleic acid, wherein the reporter group is a detectable group, and

(c) detecting the detectable group as an indication of the presence of said immobilized nucleic acid.

43. A method for in situ hybridization, comprising
(a) immobilizing a nucleic acid on a solid support to produce an immobilized nucleic acid,
(b) hybridizing a nucleic acid according to claim 18 with said immobilized nucleic acid, wherein the reporter group is a detectable group, and
(c) detecting the detectable group as an indication of the presence of said immobilized nucleic acid.

44. A method for in situ hybridization, comprising
(a) immobilizing a nucleic acid on a solid support to produce an immobilized nucleic acid,
(b) hybridizing a nucleic acid according to claim 19 with said immobilized nucleic acid, wherein the reporter group is a detectable group, and
(c) detecting the detectable group as an indication of the presence of said immobilized nucleic acid.

45. A method for in situ hybridization, comprising
(a) immobilizing a nucleic acid on a solid support to produce an immobilized nucleic acid,
(b) hybridizing a nucleic acid according to claim 20 with said immobilized nucleic acid, wherein the reporter group is a detectable group, and
(c) detecting the detectable group as an indication of the presence of said immobilized nucleic acid.

46. A method for chemically synthesizing an oligonucleotide, comprising synthesizing an oligonucleotide chain on a solid support by stepwise linking nucleosides, and cleaving said oligonucleotide chain from said solid carrier, wherein at least one of the nucleosides is a compound of formula V:

wherein
$R_1$, $R_2$ and $R_3$ are independently selected from the group consisting of hydrogen, halogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, carboxy, $C_1$-$C_6$ alkyl, $C_2$-$C_6$ alkenyl, $C_2$-$C_6$ alkynyl, $C_6H_5$—, —O—$(CH_2)_n CH_3$ wherein n=0–6, —O—$C_6H_5$, —$(CH_2)_n C_6H_5$ wherein n=1–6, —O—$(CH_2)_n C_6H_5$ wherein n=1–6, and a reporter group, $R_5$ and $R_6$ are independently selected from the group consisting of hydrogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, —O—$(CH_2)_n CH_3$ wherein n=0–6, —O—$C_2$-$C_6$ alkenyl, —O—$C_2$-$C_6$ alkynyl, a protecting group and a reporter group, $R_7$ is a phosphoramidite or H-phosphonate group,

$R_8$ is selected from the group consisting of hydrogen or a hydroxy, thio, —$(CH_2)_n$—SH wherein n=1–10, —S—$(CH_2)_n CH_3$ wherein n=0–10, an amino group, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, and —C≡C—$(CH_2)_n$—$NH_2$ wherein n=1–10, and $R_9$ is a protecting group, or a tautomer or salt thereof, wherein at least one of $R_1$, $R_2$, $R_3$, $R_5$ and $R_6$ is a reporter group which is bound to the pyrimidine or furanose ring via a linker group, wherein the linker group contains an alkynyl group.

47. A method for chemically synthesizing an oligonucleotide, comprising synthesizing an oligonucleotide chain on a solid support by stepwise linking nucleosides, and cleaving said oligonucleotide chain from said solid carrier, wherein at least one of the nucleosides is a compound of formula V:

wherein
$R_1$, $R_2$ and $R_3$ are independently selected from the group consisting of hydrogen, halogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, carboxy, $C_1$-$C_6$ alkyl, $C_2$-$C_6$ alkenyl, $C_2$-$C_6$ alkynyl, $C_6H_5$—, —O—$(CH_2)_n CH_3$ wherein n=0–6, —O—$C_6H_5$, —$(CH_2)_n C_6H_5$ wherein n=1–6, —O—$(CH_2)_n C_6H_5$ wherein n=1–6, and a reporter group, $R_5$ and $R_6$ are independently selected from the group consisting of hydrogen, hydroxy, thio, —$(CH_2)_n$—SH wherein n=1–10, —S—$(CH_2)_n CH_3$ wherein n=1–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, —O—$(CH_2)_n CH_3$ wherein n=0–6, —O—$C_2$-$C_6$ alkenyl, —O—$C_2$-$C_6$ alkynyl, a protecting group and a reporter group, $R_7$ is a phosphoramidite or H-phosphonate group, $R_8$ is selected from the group consisting of hydrogen or a hydroxy, thio, —$(CH_2)_n$—SH wherein n=1–10, —S—

$(CH_2)_nCH_3$ wherein n=0–10, an amino group, —$(CH_2)_n$—$NH_2$ wherein n=1–15, —$(CH_2)_nC(=O)$—$NH_2$ wherein n=1–15, —NH—$(CH_2)_nCH_3$ wherein n=0–15, —NH—$(CH_2)_nNH_2$ wherein n=1–15, —CH=$(CH_2)_n$—$NH_2$ wherein n=1–6, and —C≡C—$(CH_2)_n$—$NH_2$ wherein n=1–10, and

$R_9$ is a protecting group, or a tautomer or salt thereof, wherein at least one of $R_1$, $R_2$, $R_3$, $R_5$ and $R_6$ is a reporter group which is bound to the pyrimidine or furanose ring via a linker group, wherein the linker group contains an ethylene glycol group.

48. A method for chemically synthesizing an oligonucleotide, comprising synthesizing an oligonucleotide chain on a solid support by stepwise linking nucleosides, and cleaving said oligonucleotide chain from said solid carrier, wherein at least one of the nucleosides is a compound of formula V:

wherein $R_1$, $R_2$ and $R_3$ are independently selected from the group consisting of hydrogen, halogen, hydroxy, thio, —$(CH_2)_n$—SH wherein n=1–10, —S—$(CH_2)_nCH_3$ wherein n=0–10, amino, —$(CH_2)_n$—$NH_2$ wherein n=1–15, —$(CH_2)_nC(=O)$—$NH_2$ wherein n=1–15, —NH—$(CH_2)_nCH_3$ wherein n=0–15, —NH—$(CH_2)_n$$NH_2$ wherein n=1–15, —CH=$(CH_2)_n$—$NH_2$ wherein n=1–6, —C≡C—$(CH_2)_n$—$NH_2$ wherein n=1–10, carboxy, $C_1$–$C_6$ alkyl, $C_2$–$C_6$ alkenyl, $C_2$–$C_6$ alkynyl, $C_6H_5$—, —O—$(CH_2)_n$—$CH_3$ wherein n=0–6, —O—$C_6H_5$, —$(CH_2)_nC_6H_5$ wherein n=1–6, —O—$(CH_2)_nC_6H_5$ wherein n=1–6, and a reporter group, $R_5$ and $R_6$ are independently selected from the group consisting of hydrogen, hydroxy, thio, —$(CH_2)_n$—SH wherein n=1–10, —S—$(CH_2)_nCH_3$ wherein n=0–10, amino, —$(CH_2)_nNH_2$ wherein n=1–15, —$(CH_2)_nC(=O)$—$NH_2$ wherein n=1–15, —NH—$(CH_2)_nCH_3$ wherein n=0–15, —NH—$(CH_2)_nNH_2$ wherein n=1–15, —CH=$(CH_2)_n$—$NH_2$ wherein n=1–6, —C≡C—$(CH_2)_n$—$NH_2$ wherein n=1–10, —O—$(CH_2)_nCH_3$ wherein n=0–6, —O—$C_2$-$C_6$ alkenyl, —O—$C_2$-$C_6$ alkynyl, a protecting group and a reporter group, $R_7$ is a phosphoramidite or H-phosphonate group, $R_8$ is selected from the group consisting of hydrogen or a hydroxy, thio, —$(CH_2)_n$—SH wherein n=1–10, —S—$(CH_2)_nCH_3$ wherein n=0–10, an amino group, —$(CH_2)_n$—$NH_2$ wherein n=1–15, —$(CH_2)_nC(=O)$—$NH_2$ wherein n=1–15, —NH—$(CH_2)_nCH_3$ wherein n=0–15, —NH—$(CH_2)_nNH_2$ wherein n=1–15, —CH=$(CH_2)_n$—$NH_2$ wherein n=1–6, and —C≡C—$(CH_2)_n$—$NH_2$ wherein n=1–10, and

$R_9$ is a protecting group, or a tautomer or salt thereof, wherein at least one of $R_1$, $R_2$, $R_3$, $R_5$ and $R_6$ is a reporter group which is bound to the pyrimidine or furanose ring via a linker group.

49. A method for chemically synthesizing an oligonucleotide, comprising synthesizing an oligonucleotide chain on a solid support by stepwise linking nucleosides, and cleaving said oligonucleotide chain from said solid carrier, wherein at least one of the nucleosides is a compound of formula V:

wherein $R_1$, $R_2$ and $R_3$ are independently selected from the group consisting of hydrogen, halogen, hydroxy, thio, —$(CH_2)_n$—SH wherein n=1–10, —S—$(CH_2)_nCH_3$ wherein n=0–10, amino, —$(CH_2)_n$—$NH_2$ wherein n=1–15, —$(CH_2)_nC(=O)$—$NH_2$ wherein n=1–15, —NH—$(CH_2)_nCH_3$ wherein n=0–15, —NH—$(CH_2)_n$$NH_2$ wherein n=1–15, —CH=$(CH_2)_n$—$NH_2$ wherein n=1–6, —C≡C—$(CH_2)_n$—$NH_2$ wherein n=1–10, carboxy, $C_1$–$C_6$ alkyl, $C_2$–$C_6$ alkenyl, $C_2$–$C_6$ alkinyl, $C_6H_5$—, —O—$(CH_2)_nCH_3$ wherein n=0–6, —O—$C_6H_5$, —$(CH_2)_nC_6H_5$ wherein n=1–6, —O—$(CH_2)_nC_6H_5$ wherein n=1–6, and a reporter group, $R_5$ and $R_6$ are independently selected from the group consisting of hydrogen, hydroxy, thio, —$(CH_2)_n$—SH wherein n=1–10, —S—$(CH_2)_nCH_3$ wherein n=0–10, amino, —$(CH_2)_nNH_2$ wherein n=1–15, —$(CH_2)_nC(=O)$—$NH_2$ wherein n=1–15, —NH—$(CH_2)_nCH_3$ wherein n=0–15, —NH—$(CH_2)_nNH_2$ wherein n=1–15, —CH=$(CH_2)_n$—$NH_2$ wherein n=1–6, —C≡C—$(CH_2)_n$—$NH_2$ wherein n=1–10, —O—$(CH_2)_nCH_3$ wherein n=0–6, —O—$C_2$-$C_6$ alkenyl, —O—$C_2$-$C_6$ alkinyl, a protecting group and a reporter group, $R_7$ is a phosphoramidite or H-phosphonate group,

$R_8$ is selected from the group consisting of hydrogen or a hydroxy, thio, —$(CH_2)_n$—SH wherein n=1–10, —S—$(CH_2)_nCH_3$ wherein n=0–10, an amino group, —$(CH_2)_n$—$NH_2$ wherein n=1–15, —$(CH_2)_nC(=O)$—$NH_2$ wherein n=1–15, —NH—$(CH_2)_nCH_3$ wherein n=0–15, —NH—$(CH_2)_nNH_2$ wherein n=1–15, —CH=$(CH_2)_n$—$NH_2$ wherein n=1–6, and —C≡C—$(CH_2)_n$—$NH_2$ wherein n=1–10, and $R_9$ is a protecting group, or a tautomer or salt thereof, wherein at least one of $R_1$, $R_2$, $R_3$, $R_5$ and $R_6$ is a reporter group which is bound to the pyrimidine or furanose ring via a linker group, wherein the linker group contains an alkynyl group and is of a sufficient length such that the compound can be incorporated into the oligonucleotide by means of a polymerase.

50. A method for chemically synthesizing an oligonucleotide, comprising synthesizing an oligonucleotide chain on a solid support by stepwise linking nucleosides, and cleaving said oligonucleotide chain from said solid carrier, wherein at least one of the nucleosides is a compound of formula V:

wherein $R_1$, $R_2$ and $R_3$ are independently selected from the group consisting of hydrogen, halogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, —C≡C—$(CH_2)_n$—$NH_2$ wherein n=1–10, carboxy, $C_1$-$C_6$ alkyl, $C_2$-$C_6$ alkenyl, $C_2$-$C_6$ alkinyl, $C_6H_5$—, —O—$(CH_2)_n CH_3$ wherein n=0–6, —O—$C_6H_5$, —$(CH_2)_n C_6H_5$ wherein n=1–6, —O—$(CH_2)_n C_6H_5$ wherein n=1–6, and a reporter group, $R_5$ and $R_6$ are independently selected from the group consisting of hydrogen, hydroxy, thio, —$(CH_2)_n$—SH wherein n=1–10, —S—$(CH_2)_n CH_3$ wherein n=0–10, amino, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n$—$NH_2$ wherein n=1–15, —CH=$(CH_2)_n NH_2$ wherein n=1–6, —C≡C—$(CH_2)_n$—$NH_2$ wherein n=1–10, —O—$(CH_2)_n CH_3$ wherein n=0–6, —O—$C_2$-$C_6$ alkenyl, —O—$C_2$-$C_6$ alkinyl, a protecting group and a reporter group, $R_7$ is a phosphoramidite or H-phosphonate group, $R_8$ is selected from the group consisting of hydrogen or a hydroxy, thio, —$(CH_2)_n$—SH wherein n=1–10, —S—$(CH_2)_n CH_3$ wherein n=0–10, an amino group, —$(CH_2)_n$—$NH_2$ wherein n=1–15, —$(CH_2)_n C(=O)$—$NH_2$ wherein n=1–15, —NH—$(CH_2)_n CH_3$ wherein n=0–15, —NH—$(CH_2)_n NH_2$ wherein n=1–15, —CH=$(CH_2)_n$—$NH_2$ wherein n=1–6, and —C≡C—$(CH_2)_n$—$NH_2$ wherein n=1–10, and $R_9$ is a protecting group, or a tautomer or salt thereof, wherein at least one of $R_1$, $R_2$, $R_3$, $R_5$ and $R_6$ is a reporter group which is bound to the pyrimidine or furanose ring via a linker group, wherein the linker group contains an ethylene glycol group and is of a sufficient length such that the compound can be incorporated into the oligonucleotide by means of a polymerase.

* * * * *